United States Patent
Ai (10) Patent No.: US 11,352,364 B2
(45) Date of Patent: Jun. 7, 2022

(54) PHTHALOCYANINE NANOSPHERE, PREPARATION METHOD THEREOF, AND COLOR FILTER

(71) Applicant: TCL China Star Optoelectronics Technology Co., Ltd., Guangdong (CN)

(72) Inventor: Lin Ai, Guangdong (CN)

(73) Assignee: TCL China Star Optoelectronics Technology Co. Ltd., Shenzhen (CN)

( * ) Notice: Subject to any disclaimer, the term of this patent is extended or adjusted under 35 U.S.C. 154(b) by 265 days.

(21) Appl. No.: 16/626,240

(22) PCT Filed: Dec. 13, 2019

(86) PCT No.: PCT/CN2019/125049
§ 371 (c)(1),
(2) Date: Dec. 23, 2019

(87) PCT Pub. No.: WO2021/103171
PCT Pub. Date: Jun. 3, 2021

(65) Prior Publication Data
US 2021/0163492 A1    Jun. 3, 2021

(30) Foreign Application Priority Data
Nov. 28, 2019 (CN) .......................... 201911186955.X (51) Int. Cl.
| | |
|---|---|
| C07D 487/22 | (2006.01) |
| C01B 32/182 | (2017.01) |
| C07F 1/08 | (2006.01) |
| C07F 3/06 | (2006.01) |
| G02B 5/20 | (2006.01) |
| B82Y 40/00 | (2011.01) |

(52) U.S. Cl.
CPC .......... *C07D 487/22* (2013.01); *C01B 32/182* (2017.08); *C07F 1/08* (2013.01); *C07F 3/06* (2013.01); *G02B 5/20* (2013.01); *B82Y 40/00* (2013.01)

(58) Field of Classification Search
CPC ...... C07D 487/22; C01B 32/182; G02B 5/20; B82Y 40/00
See application file for complete search history.

(56) References Cited

U.S. PATENT DOCUMENTS

5,998,609 A * 12/1999 Aoki ................... C09B 47/0675
428/64.1

* cited by examiner

*Primary Examiner* — Noble E Jarrell
(74) *Attorney, Agent, or Firm* — The Roy Gross Law Firm, LLC; Roy Gross (57) ABSTRACT

A method for preparing phthalocyanine nanospheres is provided, including: synthesizing an ionic phthalocyanine molecule of formula I according to a following chemical scheme:

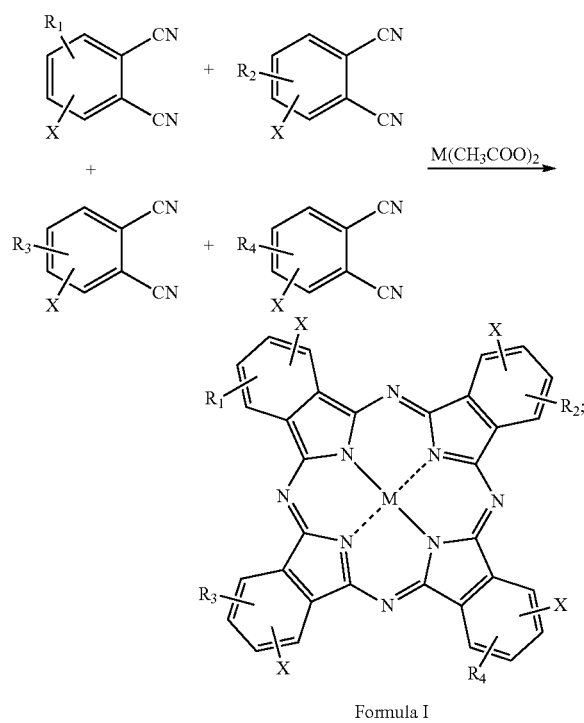

Formula I wherein M is Cu or Zn, X is Br or Cl, $R_1$, $R_2$, $R_3$, and $R_4$ are aromatic substituent groups; dissolving at least one ionic phthalocyanine molecule selected from the formula I in a solvent to form a solution; preparing a two-dimensional layer crystalline material with an opposite charge to the ionic phthalocyanine molecule; adding the two-dimensional layer crystalline material to the solution; heating the solution to evaporate a portion of the solvent to aggregate the ionic phthalocyanine molecule into phthalocyanine nanospheres between a film layer of the two-dimensional layer crystalline material; and separating the phthalocyanine nanospheres from the film layer of the two-dimensional layer crystalline material.

13 Claims, 3 Drawing Sheets

PHTHALOCYANINE NANOSPHERE, PREPARATION METHOD THEREOF, AND COLOR FILTER

FIELD OF INVENTION

The invention relates to the technical field of display panels, in particular to phthalocyanine nanospheres, a preparation method thereof, and a color filter.

BACKGROUND OF INVENTION

In the field of display technology, people continuously pursue higher color saturation. With the maturity development of high-resolution technology, there will be a significant improvement in the definition. An advantage of high-resolution is that the colors are richer, providing users with an immersive viewing experience. The benefit of high-resolution is not only more pixels, but also better pixels. High-resolution makes pixels smaller, this means less light will pass through the panel, so the pixels must become more efficient. Therefore, it is necessary to develop a color photoresist material that has high transmittance, high contrast, and wide color gamut.

Most of the green photoresist materials that contribute the most transmittance in color filters are phthalocyanine molecular compounds. Because a macrocyclic conjugate plane structure of the phthalocyanine molecular compounds is prone to aggregate to form large crystals, the currently used pigment particles are mechanically dispersed.

Technical Problem

Most of the green photoresist materials that contribute the most transmittance in color filters are phthalocyanine molecular compounds. Because a macrocyclic conjugate plane structure of the phthalocyanine molecular compounds is prone to aggregate to form large crystals, the currently used pigment particles are mechanically dispersed. The steps of this preparation method are complicated, and each step will affect the optical property of the color filters. In addition, the sizes of the prepared particles are large, and the distribution of the particle sizes is not uniform, resulting in lower brightness and contrast. Therefore, there is an urgent need for a better preparation method of phthalocyanine molecular nanoscale crystals.

SUMMARY OF INVENTION

In order to solve the problem existing in the prior art for preparing the photoresist materials, that is: due to the large particle size and ununiform distribution of the particle size, which cause displays to have low brightness and contrast. The present invention provides a method for preparing phthalocyanine nanospheres, the preparation method is:

synthesizing ionic phthalocyanine molecules of formula I according to a following chemical scheme:

Formula I wherein M is Cu or Zn, X is Br or Cl, and $R_1$, $R_2$, $R_3$, and $R_4$ are each independently selected from one of:

, and

Formula I dissolving the ionic phthalocyanine molecules selected from at least one chemical structure of the formula I in a solvent to form a solution; preparing graphene flakes with an opposite charge to the ionic phthalocyanine molecules; adding the graphene flakes to the solution; heating the solution to evaporate a portion of the solvent to aggregate the ionic phthalocyanine molecules into phthalocyanine nanospheres between film layers of the graphene flakes; and purifying and separating the phthalocyanine nanospheres from the film layers of the graphene flakes.

Preferably, the method for preparing the graphene flakes includes following steps:

providing a metal as a cathode and a graphene rod as an anode, and placing the metal and the graphene rod in a container containing an electrolyte solution and conductive ions; and applying current to the metal and the graphene rod with a direct current (DC) voltage to cause the electrolyte solution generating a gas; and the gas and the conductive ions penetrate into an interlayer gap of the graphene rod so that the graphene rod forms the graphene flakes having a two-dimensional layer structure.

Preferably, the metal is platinum.

Preferably, the DC voltage is 5 volts (V), and the two-dimensional layer structure of the graphene flakes has an interlayer distance between 20 nm and 40 nm.

Preferably, the interlayer distance of the two-dimensional layer structure is adjusted by changing a magnitude of the DC voltage.

The invention further provides another method for preparing phthalocyanine nanospheres, the preparation method is as follows:

synthesizing ionic phthalocyanine molecules of formula I according to a following chemical scheme:

wherein M is Cu or Zn, X is Br or Cl, and $R_1$, $R_2$, $R_3$, and $R_4$ are aromatic substituent groups; dissolving the ionic phthalocyanine molecule selected from at least one chemical structure of the formula I in a solvent to form a solution; preparing a two-dimensional layer crystalline material with an opposite charge to the ionic phthalocyanine molecules; adding the two-dimensional layer crystalline material to the solution; heating the solution to evaporate a portion of the solvent to aggregate the ionic phthalocyanine molecules into phthalocyanine nanospheres between film layers of the two-dimensional layer crystalline material; and purifying and separating the phthalocyanine nanospheres from the film layers of the two-dimensional layer crystalline material.

Preferably, the $R_1$, $R_2$, $R_3$ and $R_4$ are each independently selected from one of

, and

Preferably, the ionic phthalocyanine molecule is selected from at least one of -continued Preferably, the two-dimensional layer crystalline material is graphene flake.

Preferably, the method for preparing the graphene flakes comprises following steps:

providing a metal as a cathode and a graphene rod as an anode, and placing the metal and the graphene rod in a container containing an electrolyte solution and conductive ions; and applying current to the metal and the graphene rod with a DC voltage to cause the electrolyte solution generating a gas; the gas and the conductive ion penetrate into an interlayer gap of the graphene rod so that the graphene rod forms the graphene flakes having a two-dimensional layer structure.

Preferably, the DC voltage is 5 volts (V), and the two-dimensional layer structure of the graphene flakes has an interlayer distance between 20 nm and 40 nm.

Preferably, the interlayer distance of the two-dimensional layer structure is adjusted by changing a magnitude of the DC voltage.

The present invention further provides a phthalocyanine nanosphere, including a group selected from following ionic phthalocyanine molecules:

wherein M is Cu or Zn, X is Br or Cl, $R_1$, $R_2$, $R_3$, and $R_4$ are each independently selected from one of:

Preferably, a particle size of the phthalocyanine nanosphere is between 10 and 30 nm.

The present invention also provides a color filter, including:

a substrate and a photoresist layer disposed on the substrate, the photoresist layer including the phthalocyanine nanosphere described above.

Beneficial Effect

The phthalocyanine nanospheres obtained by the preparation method of the present invention are used as a color material of a color photoresist layer. Due to the small and uniform particle size of the phthalocyanine nanospheres, the transmittance and contrast of the color photoresist layer are greatly improved. The prepared color photoresist layer is used for a liquid crystal display, and a display performance of the liquid crystal display can be optimized to match high-resolution display requirements.

DETAILED DESCRIPTION OF PREFERRED EMBODIMENTS

The technical solutions in the embodiments of the present invention will be clearly and completely described with reference to the accompanying drawings in the embodiments of the present invention. Obviously, the described embodiments are only a part of the embodiments of the present invention, but not all the embodiments. Based on the embodiments of the present invention, all other embodiments obtained by those skilled in the art without creative activity fall into the protection scope of the present application.

Figure 1:
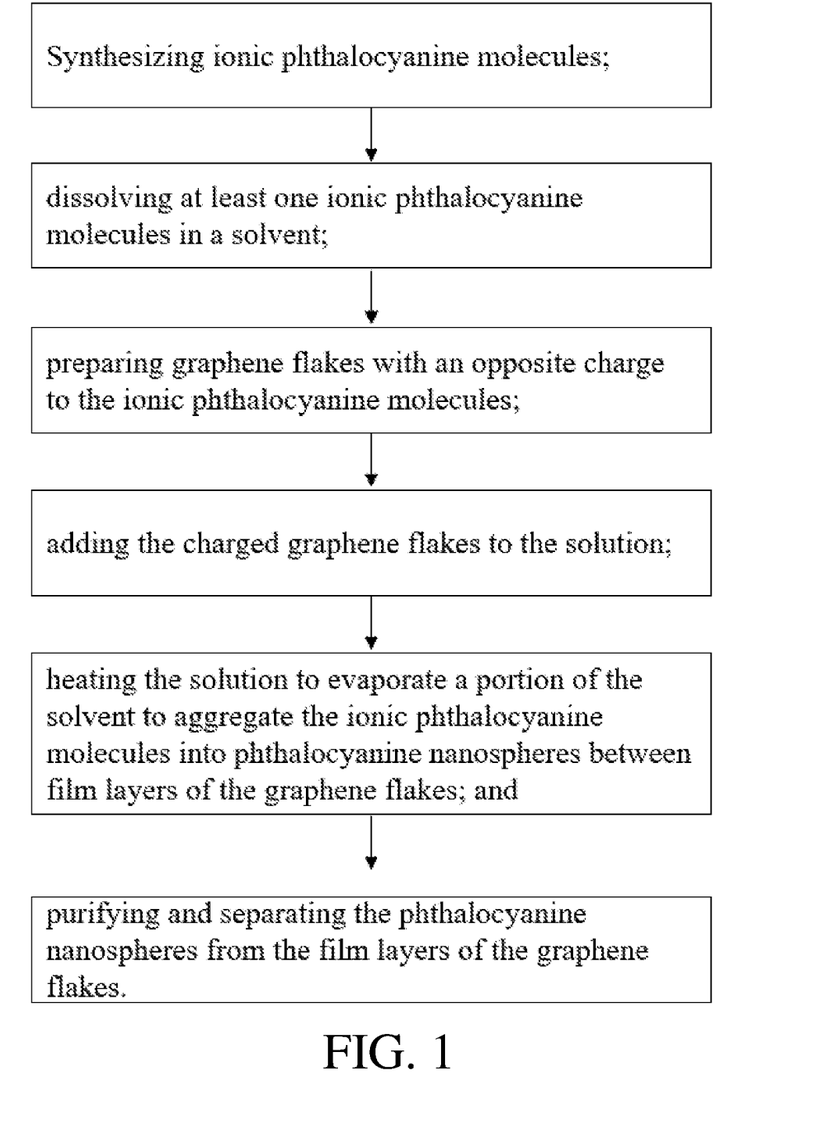
FIG. 1 is a flowchart of a method for preparing phthalocyanine nanospheres according to an embodiment of the present invention.

A preferred embodiment of the present invention provides a method for preparing phthalocyanine nanospheres. As shown in the flowchart in FIG. 1, including: synthesis of ionic phthalocyanine molecules, preparation of charged graphene flakes, and preparation of phthalocyanine nanospheres. The phthalocyanine nanosphere can be applied to the preparation of a color photoresist layer in a color filter.

A preferred embodiment of the present invention synthesizes three ionic phthalocyanine molecules. As shown below, the ionic phthalocyanine molecule is synthesized by tetramerization, and the specific synthesis process is:

In a nitrogen ($N_2$) environment, the phthalocyanine precursors, and metal acetic acid ($M(CH_3COO)_2$) are heated under reflux in a high boiling point alcohol solvent for 5 days. Adding 1,8-diazabicyclo [5.4.0]undec-7-ene (DBU) as a catalyst, after the reaction is completed and purified by column chromatography, the target ionic phthalocyanine molecules can be obtained, wherein M is Cu or Zn; the ionic phthalocyanine molecule is synthesized according to the following chemical scheme:

wherein the metal M can be Cu or Zn; X is one or more of Br and Cl, it is used to adjust the chromaticity of phthalocyanine molecules. When the compound is synthesized, the substituents $R_1$, $R_3$, and $R_4$ are the substituent $R_2$ is an addition ratio of and

-continued is 3:1;
when the compound is is synthesized, the substituents $R_1$, $R_3$, and $R_4$ are the substituent $R_2$ is an addition ratio of is 3:1; and when the compound is synthesized, $R_1$ and $R_2$ are

$R_3$ is and $R_4$ is an addition ratio of is 2:1:1.

Figure 2:
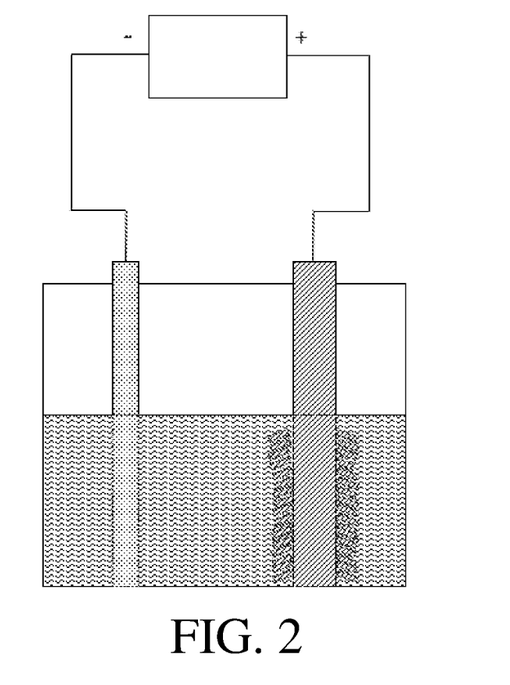
FIG. 2 is a schematic diagram of the preparation of charged graphene flakes according to an embodiment of the present invention.

In an embodiment of the present invention, the charged graphene flakes are prepared by an electrochemical stripping method, a high-purity graphite rod is used as anodes, a platinum metal is used as the cathode, water or sodium sulfate aqueous solution is used as the electrolyte solution, and tetrabutylammonium hexafluorophosphate is added as the conductive ion, and the current is applied to at a direct current (DC) voltage of 5 volts. Please refer to FIG. 2. It can be seen that graphene flakes are dissociated in the electrolyte solution. After 3 minutes, gas is generated from the electrolyte solution, and the gas and ionic groups penetrate into the graphene flakes to make it unfold, and graphene flakes with an interlayer distance of about 30 nm are obtained. If water is used as the electrolyte solution, the obtained graphene flakes are positively charged; if an aqueous sodium sulfate solution is used as the electrolyte solution, the obtained graphene flakes will adsorb sulfate ions, that is, the obtained graphene flakes are negatively charged. The distance between graphene flakes can be controlled by changing the magnitude of the direct current (DC) voltage and the time of applying current, and objects of regulating the electric charge between the graphene flakes and the distance between the layers thereof are achieved.

Figure 3:
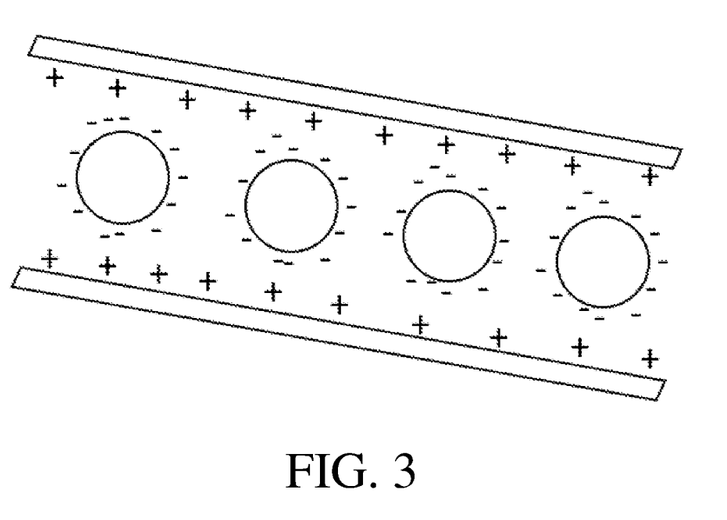
FIG. 3 is a schematic diagram of phthalocyanine nanospheres formed between graphene flakes according to an embodiment of the present invention.

The synthesized ionic phthalocyanine molecule is dissolved in an ethyl acetate solution, and formulated into a 0.5M solution, which is stirred and dissolved uniformly, then adding the prepared charged graphene flakes and heating the solution. The enhanced electrostatic attraction between phthalocyanine molecules and graphene flakes during solution evaporation promotes the non-oriented aggregation of phthalocyanine molecules into microspheres between graphene flakes, which can be completed until the solution is half evaporated.

Please refer to FIG. 3, as microspheres aggregated into phthalocyanine molecules and continue to grow up, the accumulation of charges around the microspheres increases, and the repulsive force between the microspheres and the phthalocyanine molecules increases. At this time, the microspheres aggregated by phthalocyanine molecules no longer grow up, and then the microspheres with uniform size are formed. Next, the obtained phthalocyanine microspheres are purified and separated, a slight ultrasonic wave is used to destroy the electrostatic force, and then centrifuged in a centrifuge at 1500 rpm/min for 3 minutes, the nano-scale phthalocyanine microspheres can be separated from the micro-scale graphene flakes.

As described above, the type of charge carried by graphene flakes can be determined by controlling the type of electrolyte solution, and also the type of charge carried by the ionic phthalocyanine molecule can be controlled by selecting the ionic group connected to the phthalocyanine molecule. When preparing phthalocyanine nanospheres with uniform particle size, the charge type of the flake template and the charge type of the phthalocyanine molecule should be designed to be opposite. In addition, the charge amount of phthalocyanine nanospheres can be controlled by controlling the number of ionic ligands introduced. By controlling the size of the steric hindrance of the substituents, that is, the degree of repulsion, the particle size of the phthalocyanine nanospheres can be controlled. As described by the embodiment of the present invention, phthalocyanine nanospheres with a uniform particle size of a range of 10-30 nm can be obtained.

The phthalocyanine nanospheres with uniform particle size obtained above are dissolved in propylene glycol methyl ether acetate (PGMEA) solvent, and coated by adding a stabilizer with opposite charge to neutralize their charges and improve their storage stability, and mix them with photoinitiator, polymer resin (such as acrylic resin), monomers, etc. in a proper proportion to formulate a green photoresist solution. Next, the green photoresist solution and other color photoresist solution are coated on a glass substrate. Then, processes such as pre-baking to remove solvent, exposure, and development are performed. Finally, post-baking curing is performed to complete the preparation of the color photoresist layer.

Figure 4:
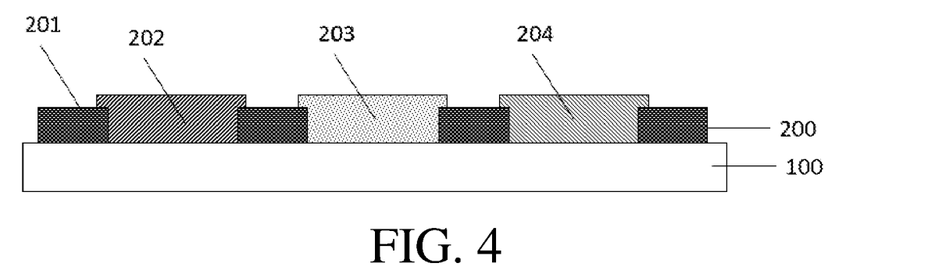
FIG. 4 is a schematic diagram of a color filter according to an embodiment of the present invention.

As shown in FIG. 4, the color photoresist layer 200 includes a black matrix 201, a red photoresist layer 202, a green photoresist layer 203, and a blue photoresist layer 204. The green photoresist layer 203 includes the phthalocyanine nanospheres according to the embodiment of the present invention. Because the small and uniform particle size of the color-developing material, the transmittance and contrast of the color photoresist layer 200 are greatly improved. Applying the prepared color photoresist layer to a liquid crystal display can optimize its display performance to match the display requirements of 8K resolution.

The description of the above exemplary embodiments is only for the purpose of understanding the invention. It is to be understood that the present invention is not limited to the disclosed exemplary embodiments. It is obvious to those skilled in the art that the above exemplary embodiments may be modified without departing from the scope and spirit of the present invention.

What is claimed is:

1. A method for preparing phthalocyanine nanospheres, comprising:
    synthesizing ionic phthalocyanine molecules of formula I according to a following chemical scheme:

Formula I wherein M is Cu or Zn, X is Br or Cl, and $R_1$, $R_2$, $R_3$, and $R_4$ are each independently selected from one of:

, and dissolving the ionic phthalocyanine molecules selected from at least one chemical structure of the formula I in a solvent to form a solution;
preparing graphene flakes with an opposite charge to the ionic phthalocyanine molecules;
adding the graphene flakes to the solution;
heating the solution to evaporate a portion of the solvent to aggregate the ionic phthalocyanine molecules into phthalocyanine nanospheres between film layers of the graphene flakes; and
purifying and separating the phthalocyanine nanospheres from the film layers of the graphene flakes.

2. The method according to claim 1, wherein the method for preparing the graphene flakes comprises following steps:
providing a metal as a cathode and a graphene rod as an anode, and placing the metal and the graphene rod in a container containing an electrolyte solution and conductive ions; and
applying current to the metal and the graphene rod with a DC voltage to cause the electrolyte solution generating a gas; and the gas and the conductive ions penetrate into an interlayer gap of the graphene rod so that the graphene rod forms the graphene flakes having a two-dimensional layer structure.

3. The method according to claim 2, wherein the metal is platinum.

4. The method according to claim 2, wherein the DC voltage is 5V, and the two-dimensional layer structure of the graphene flakes has an interlayer distance between 20 nm and 40 nm.

5. The method according to claim 2, wherein the interlayer distance of the two-dimensional layer structure is adjusted by changing a magnitude of the DC voltage.

6. A method for preparing phthalocyanine nanospheres, comprising:
synthesizing ionic phthalocyanine molecules of formula I according to a following chemical scheme:

Formula I wherein M is Cu or Zn, X is Br or Cl, and $R_1$, $R_2$, $R_3$, and $R_4$ are each independently selected from one of:

-continued dissolving the ionic phthalocyanine molecule selected from at least one chemical structure of the formula I in a solvent to form a solution;

preparing a two-dimensional layer crystalline material with an opposite charge to the ionic phthalocyanine molecules;

adding the two-dimensional layer crystalline material to the solution;

heating the solution to evaporate a portion of the solvent to aggregate the ionic phthalocyanine molecules into phthalocyanine nanospheres between film layers of the two-dimensional layer crystalline material; and purifying and separating the phthalocyanine nanospheres from the film layers of the two-dimensional layer crystalline material.

7. The method according to claim 6, wherein the two-dimensional layer crystalline material is graphene flakes.

8. The method according to claim 7, wherein the method for preparing the graphene flakes comprises following steps:

providing a metal as a cathode and a graphene rod as an anode, and placing the metal and the graphene rod in a container containing an electrolyte solution and conductive ions; and applying current to the metal and the graphene rod with a DC voltage to cause the electrolyte solution generating a gas; the gas and the conductive ion penetrate into an interlayer gap of the graphene rod so that the graphene rod forms the graphene flakes having a two-dimensional layer structure.

9. The method according to claim 8, wherein the DC voltage is 5V, and the two-dimensional layer structure of the graphene flakes has an interlayer distance between 20 nm and 40 nm.

10. The method according to claim 8, wherein the interlayer distance of the two-dimensional layer structure is adjusted by changing a magnitude of the DC voltage.

11. A phthalocyanine nanosphere, comprising a group selected from following ionic phthalocyanine molecules:

wherein M is Cu or Zn, X is Br or Cl, $R_1$, $R_2$, $R_3$, and $R_4$ are each independently selected from one of:

12. The phthalocyanine nanosphere according to claim 11, wherein a particle size of the phthalocyanine nanosphere is between 10 and 30 nm.

13. A color filter, comprising:
a substrate and a photoresist layer disposed on the substrate, the photoresist layer comprising the phthalocyanine nanosphere according to claim 11.

* * * * *